United States Patent
Merrill et al.

(10) Patent No.: US 6,284,274 B1
(45) Date of Patent: Sep. 4, 2001

(54) ANALGESIC TABLET COMPOSITIONS

(75) Inventors: Sonya Merrill, San Jose; Atul D. Ayer, Palo Alto; Paul M. Hwang; Anthony L. Kuczynski, both of Mountain View; Nils W. Ahlgren, Sunnyvale; Deborah J. Johnson, Fremont, all of CA (US)

(73) Assignee: Alza Corporation, Mt. View, CA (US)

( * ) Notice: Subject to any disclaimer, the term of this patent is extended or adjusted under 35 U.S.C. 154(b) by 0 days.

(21) Appl. No.: 09/518,584

(22) Filed: Mar. 3, 2000

Related U.S. Application Data

(62) Division of application No. 09/333,380, filed on Jun. 15, 1999, now Pat. No. 6,077,538, which is a division of application No. 08/808,147, filed on Feb. 28, 1997, now Pat. No. 5,948,787.

(51) Int. Cl.⁷ ............... A61K 9/24; A61K 9/20; A61K 9/22
(52) U.S. Cl. ............ 424/472; 424/464; 424/468
(58) Field of Search ............... 424/464, 472, 424/468

(56) References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,201 | 9/1978 | Theeuwes | 128/260 |
| 4,111,202 | 9/1978 | Theeuwes | 128/260 |
| 4,327,725 | 5/1982 | Cortese et al. | 128/260 |
| 4,464,378 | 8/1984 | Hussain | 424/260 |
| 4,576,604 | 3/1986 | Guittard et al. | 604/890 |
| 4,612,008 | 9/1986 | Wong et al. | 604/892 |
| 4,940,588 | 7/1990 | Sparks et al. | 424/490 |
| 4,968,507 | 11/1990 | Zentner et al. | 424/465 |
| 5,021,053 | 6/1991 | Barclay et al. | 604/892.1 |
| 5,128,143 | 7/1992 | Baichwal et al. | 424/464 |
| 5,186,942 | 2/1993 | Deters et al. | 424/473 |
| 5,240,933 | 8/1993 | Merz et al. | 514/282 |

FOREIGN PATENT DOCUMENTS

| | | |
|---|---|---|
| 0377518 | 6/1989 | (EP) . |
| 2140687A | 12/1984 | (GB) . |

*Primary Examiner*—William R. A. Jarvis
(74) *Attorney, Agent, or Firm*—Paul B. Simboli; John A. Dhuey; Steven F. Stone

(57) ABSTRACT

An opiate analgesic composition and a non-opiate analgesic composition are disclosed for delivering an analgesic in either embodiment to a patient in need of relief from pain. The analgesics are present optionally with a nonionic surfactant and with an osmotic composition comprising a carbonate or bicarbonate for delivering the opiate analgesic and non-opiate analgesic from a dosage form.

5 Claims, No Drawings

ANALGESIC TABLET COMPOSITIONS

CROSS REFERENCE TO RELATED APPLICATIONS

This application is a divisional of U.S. application Ser. No. 09/333,380 filed Jun. 15, 1999, now U.S. Pat. No. 6,077,538, which is a divisional of U.S. application Ser. No. 08/808,147 filed Feb. 28, 1997, now U.S. Pat. No. 5,948,787.

FIELD OF THE INVENTION

This invention pertains to a novel dosage form for the delivery of opiate and non-opiate analgesics. The invention concerns also a dosage form comprising a composition of matter that provides for a high dose of the analgesic in the dosage form, which analgesic is delivered at a controlled rate over an extended time. The invention relates additionally to a composition of matter for use in a dosage form for delivering the analgesic to produce the analgesic effect. The invention concerns further a method of administering the dosage form for delivering the analgesic to produce an analgesic effect in a patient in need of analgesia.

BACKGROUND OF THE INVENTION

Pain is a universal experience; everyone knows what is meant by pain. To relieve pain in patients, opiate analgesics and non-opiate analgesics are administered for their therapeutic purpose. These analgesics are used to relieve pain by acting centrally to elevate pain threshold, usually without disturbing consciousness and usually without altering sensory modalities. Presently, both pharmacy and medicine administer multidoses of these analgesics for the relief of pain, as a dosage form comprising a long-term dose administered at a controlled rate over time appears to be absent in the pharmaceutical and medicinal arts.

SUMMARY OF THE INVENTION

In view of the foregoing, it is readily apparent that a serious need exists for an improvement for delivering opiate analgesics and for delivering non-opiate analgesics for their therapeutic effect. Thus, it is an immediate object of the present invention to provide a dosage form that comprises a drug analgesic composition present as a layer containing a therapeutic dose of a member selected from the group consisting of an opiate analgesic and non-opiate analgesic, which in either analgesic manufacture is administered in a preferred, essentially zero-order dose over an extended time for their therapeutic effect. Further, it is an object of the present invention to provide a novel composition of matter, manufactured as an osmotic composition in a layer, with fluid imbibing properties for expanding and pushing the opiate analgesic or non-opiate analgesic at a controlled rate over time from the dosage form.

DETAILED DESCRIPTION OF THE INVENTION

The terms "analgesic" and "analgesic drug" as used for the purpose of this invention denote an active agent that relieves pain in humans and in animals. The expression "opiate analgesic" denotes a narcotic analgesic used, for example, as an adjunct to anesthesia, to alleviate sharp pain of traumatic origin, to alleviate pain of visceral origin, in surgery, for chronic pain caused by disease and the like. The expression "non-opiate analgesic" denotes a nonnarcotic agent indicated for aches, pains of headaches and the like. Representatives of an opiate analgesic comprise a member selected from the group consisting of morphine, codeine, hydrocodone, hydromorphone, levorphanol, oxymorphone and levallorphan. The non-opiate analgesics are represented by a member selected from the group consisting of: alfentanil, buprenorphine, butorphanol, fentanyl, meperidine, methadone, propoxyphene, pentazocine, propoxyphene, sufentanil, acetaminophen, aspirin, ibuprofen and naproxen. The active analgesic can be present as the pharmaceutically acceptable salt, such as hydrobromide, hydrochloride, mucate, sulfate, acetate, phosphate, acetate trihydrate, bi(heptafluorobutyrate), bi(methylcarbamate), bi(pentafluoropropionate), maleate, bi(pyridine-3-carboxylate), bi(trifluoroacetate), bitartrate, chlorhydrate, sulfate pentahydrate, fumarate, sodium and calcium. The analgesic composition provided by this invention comprises 50 ng to 1000 mg of the opiate analgesic or the non-opiate analgesic and zero to 10 wt % (weight-percent) of a nonionic surfactant. The osmotic composition provided by this invention comprises zero to 60 wt % of an osmagent comprising a gas generating group.

EXAMPLES OF THE INVENTION

Example 1

A novel therapeutic composition comprising the opiate analgesic morphine, wherein morphine is a member selected from the group consisting of morphine base and morphine pharmaceutically acceptable salt, was prepared as follows: first, 60.0 g of morphine sulfate pentahydrate, 79.5 g of poly(ethylene oxide) of 200,000 number-average molecular weight, available from Union Carbide Co., Institute, W. Va., and 9 g of poly(vinyl pyrrolidone) having a viscosity-average molecular weight of 40,000, available from ISP Technologies, Texas City, Tex., were blended homogeneously in a blender at low speed for two minutes. Next, 30 ml of anhydrous ethanol was slowly added over approximately one minute, followed by blending all the ingredients slowly to produce a homogenous composition. The composition was dried overnight and then passed through a 0.0331 in. (0.84 mm) screen. Then, 0.07 g of butylated hydroxytoluene was blended into the composition for one minute, followed by 1.43 g of lubricant magnesium stearate blended into the composition for approximately one minute. Next, the composition was compressed into a tablet, adapted as a layer for use in a dosage form, under one-ton compression force, with each tablet comprising 284 mg of the opiate analgesic composition. The 284 mg composition comprises 40 wt % morphine sulfate pentahydrate, 53 wt % poly(ethylene oxide), 6 wt % poly(vinyl pyrrolidone), 0.95 wt % magnesium stearate, and 0.05 wt % butylated hydroxytoluene.

Example 2

A novel composition comprising fluid-imbibing and push properties was prepared as follows: first, 159.2 g of poly(ethylene oxide) of 7,000,000 number-average molecular weight, available from Union Carbide, Institute, W. Va., 75 g of sodium bicarbonate, 12.5 g of hydroxypropylmethylcellulose of 11,200 number-average molecular weight, available from Dow Chemical Co., Midland, Mich., and 2.5 g green ferric oxide were blended at low speed for three minutes to produce a homogenous blend. Then, 100 ml of anhydrous ethanol was added to the dry blend and the ingredients blended for two minutes to yield a wet granulation. The wet granulation was passed through a 0.0469 in. (1.19 mm) screen. The screened granulation was dried overnight and then screened through a 0.0331 in. (0.84 mm) screen. Then, 0.2 g of butylated hydroxytoluene was blended into the granulation for one minute. Finally, 0.62 g of magnesium stearate was blended into the screened granulation for one minute to produce an osmotic composition. The composition was compressed into 189-mg tablets, comprising 120.3 mg of poly(ethylene oxide), 56.7 mg of sodium bicarbonate, 9.5 mg of hydroxypropylmethylcellulose total, 1.9 mg of green ferric oxide, 0.5 mg of magnesium stearate and 0.2 mg of butylated hydroxytoluene.

Example 3

A novel composition comprising fluid-imbibing and push properties was prepared as follows: first, 159.2 g of poly(ethylene oxide) of 7,000,000 number-average molecular weight, available from Union Carbide Co., Institute, W. Va., 12.5 g of hydroxypropylmethylcellulose of 11,200 number-average molecular weight, available from Dow Chemical Co., Midland, Mich., and 2.5 g green ferric oxide were blended at low speed for three minutes to produce a homogenous blend. Then, 100 ml of anhydrous ethanol was added to the dry blend and the ingredients blended for two minutes to yield a wet granulation. The wet granulation was passed through a 0.0469 in. (1.19 mm) screen. The screened granulation was dried overnight and then screened through a 0.0331 in. (0.84 mm) screen. Then, 0.2 g of butylated hydroxytoluene was blended into the granulation for one minute. Finally, 0.62 g of magnesium stearate was blended into the screened granulation for one minute to produce an osmotic composition. The composition was compressed into 189 mg tablets comprising 120.3 mg of poly(ethylene oxide), 9.5 mg of hydroxypropylmethylcellulose total, 1.9 mg of green ferric oxide, 0.5 mg of magnesium stearate, and 0.2 mg of butylated hydroxytoluene.

Example 4

A dosage form was provided by the invention as follows: first, the opiate morphine tablets and the osmotic tablets were compressed in contacting layered arrangement to provide a bilayered core. The bilayered core was coated with a semipermeable wall forming composition. The semipermeable composition comprised 95:5 (weight:weight) cellulose acetate having an acetyl content of 39.8% and polyethylene glycol having a viscosity-average molecular weight of 3,350. The two composition-forming components were dissolved in a 95:5 (weight:weight) mixture of a acetone and water at 4% solid. The average wet semipermeable membrane surrounding the core was 30 mg. Three 30 mil (0.76 mm) orifices were drilled through the semipermeable membrane connecting the opiate morphine composition with the exterior of the dosage form. Finally, the dosage forms were dried overnight at 45° C. The dosage form had a morphine mean-release rate of 7 mg/hr with a nominal T80 of 16.0 hours.

Example 5

The procedure of Example 1 is followed in this example to provide a therapeutic analgesic composition comprising 50 ng to 1000 mg of an opiate analgesic selected from the group consisting of hydrocodone, hydromorphone, levorphanol, oxymorphone and levallorphan; 35 to 275 mg of a poly(ethylene oxide) comprising a 100,000 to 350,000 number-average molecular weight; 0.5 to 50 mg of poly(vinyl pyrrolidone) of 7,500 to 225,000 viscosity-average molecular weight; zero to 10 mg of a nonionic surfactant selected from the group consisting of: polyoxyethylene fatty alcohol esters, sorbitan fatty acid esters, polyoxyethylene sorbitan fatty acid esters, polyoxyethylene sorbitan monolaurate, polyoxyethylene sorbitan monostearate, polyoxyethylene sorbitan monooleate, polyoxyethylene sorbitan monopalmitate and polyoxyethylene sorbitan monolaurylsulphate; 0.01 to 0.5 mg of butylated hydroxytoluene (0.05% bHT); and 0.1 to 10 mg of a lubricant represented by a member selected from the group consisting of magnesium stearate, calcium stearate, potassium oleate, stearic acid and sodium stearate. The therapeutic composition can contain other components, for example, colorants, compression aids and binders. The composition can be compressed at ⅛- to 3.5-ton force compression to yield the orally administrable tablet containing the opiate analgesic.

Example 6

A novel osmotic composition is prepared according to the procedure of Example 2. The composition comprises 30 to 225 mg of a cellulose polymer selected from the group consisting of sodium carboxymethylcellulose, potassium carboxymethylcellulose and calcium carboxymethylcellulose of 75,000 to 2,500,000 weight-average molecular weight, available from Aqualon Co., Hopewell, Va.; 25 to 150 mg of an osmotic nontoxic metal carbonate and bicarbonate salt, such as alkali metal carbonates and bicarbonates, and the alkaline earth carbonates and bicarbonates selected from the group consisting of lithium carbonate, sodium carbonate, potassium carbonate, lithium bicarbonate, sodium bicarbonate, potassium bicarbonate, magnesium carbonate, calcium carbonate and magnesium bicarbonate; 1 to 30 mg of a hydroxypropylmethylcellulose having a 9,200 to 125,000 number-average molecular weight; 1 to 30 mg of a hydroxypropylcellulose of 7,500 to 125,000 number-average molecular weight; 0.1 to 7.5 mg of ferric oxide; and 0.1 to 3.0 mg of a lubricant, such as magnesium stearate. The composition can be compressed at ⅛- to 3.5-ton force compression to yield a tablet for use in a dosage form.

Example 7

A novel osmotic composition is prepared according to the procedure of Example 2. The composition comprises 30 to 225 mg of a cellulose polymer, selected from the group consisting of sodium carboxymethylcellulose, potassium carboxymethylcellulose and calcium carboxymethylcellulose of 75,000 to 2,500,000 weight-average molecular weight, available from Aqualon Co., Hopewell, Va.; 1 to 30 mg of a hydroxypropylcellulose of 7,500 to 125,000 viscosity-average molecular weight; 0.1 to 7.5 mg of ferric oxide; and 0.1 to 3.0 mg of a lubricant, such as magnesium stearate. The composition can be compressed at ⅛- to 3.5-ton force compression to yield a tablet for use in a dosage form.

Example 8

An analgesic composition is provided by following the above examples, except in this example the composition comprises a non-opiate analgesic selected from the group consisting of: alfentanil, buprenorphine, fentanyl, butorphanol, meperidine, methadone, nalbuphine, sufentanil and naproxen.

Examples 9 and 10

The dosage form provided by the invention can comprise a semipermeable wall, also disclosed as a semipermeable membrane, consisting of 65 to 100 wt % of a cellulose polymer that comprises a member selected from the group consisting of: a cellulose ester, a cellulose diester, a cellulose triester, a cellulose ether, a cellulose ester-ether, a cellulose acylate, a cellulose diacylate, a cellulose triacylate, a cellulose acetate and a cellulose acetate butyrate. The semipermeable wall can comprise 0 to 40 wt % of a cellulose ether member selected from the group consisting of hydroxypropylcellulose and hydroxypropylmethylcellulose, and from 0 to 20 wt % of polyethylene glycol. The total amount of all components comprising the semipermeable wall is equal to 100 wt %. Semipermeable polymers useful for manufacturing a wall of a dosage form are disclosed in U.S. Pat. Nos. 3,845,770; 3,916,899; 4,008,719; 4,036,228 and 4,111,201. These patents are assigned to the ALZA Corporation of Palo Alto, Calif., the assignee of this patent application.

The dosage form can comprise a semipermeable wall, in additional manufactures, which comprises the selectively permeable cellulose ether, ethyl cellulose. The ethyl cellulose comprises an ethoxy group with the ethyl cellulose exhibiting a degree of substitution (DS) of about 1.4 to 3, equivalent to 40 to 50% ethoxy content, and a viscosity range of 7 to 100 centipoise or higher. More specifically, the wall comprises 45 to 80 wt % ethyl cellulose, from 5 to 30 wt % hydroxypropylcellulose, and from 5 to 30 wt % polyethylene glycol, with the total weight percent of all components comprising the wall equal to 100 wt %. In another embodiment, the wall comprises 45 to 80 wt % ethylcellulose, from 5 to 30 wt % hydroxypropylcellulose, from 2 to 20 wt % poly(vinyl pyrrolidone), with the total amount of all components comprising the wall equal to 100 wt %. The ethylcellulose polymer is known in U.S. Pat. No. 4,519,801, assigned to the ALZA Corporation of Palo Alto, Calif.

Example 11

The dosage forms provided by the invention comprise a drug analgesic compositional layer, 50 ng to 1000 mg of a member selected from the group consisting of an opiate analgesic and a non-opiate analgesic; 35 to 75 mg of a member selected from the group consisting of a poly (alkylene oxide), a poly(ethylene oxide) and a poly (propylene oxide) possessing a 100,000 to 650,000 number-average molecular weight, or a member selected from the group consisting of carboxymethylcellulose, sodium carboxymethylcellulose or potassium carboxymethylcellulose possessing a 10,000 to 400,000 weight-average molecular weight; 0.5 to 50 mg of poly(vinyl pyrrolidone) of 7,500 to 225,000 viscosity-average molecular weight; 0.0 to 50 mg of a hydroxypropylcellulose of 7,500 to 125,000 number-average molecular weight or a hydroxypropylalkylcellulose of 9,200 to 125,000 number-average molecular weight; 0 to 10 mg of a nonionic surfactant; and 0.25 to 10 mg of a lubricant; and, a push composition layer comprising: 100 to 200 mg of a member selected from the group consisting of a poly(alkylene oxide) and poly(ethylene oxide) of 3,000,000 to 10,000,000 number-average molecular weight, or 100 to 200 mg of an alkali carboxymethylcellulose of 450,000 to 2,500,000 weight-average molecular weight; 2 to 125 mg of an osmagent, selected from the group consisting of sodium bicarbonate, potassium bicarbonate and lithium bicarbonate; 0 to 30 mg of a hydroxyalkylcellulose, selected from the group consisting of hydroxyethylcellulose, hydroxypropylcellulose, hydroxyisopropylcellulose and hydroxybutylcellulose; 1 to 80 mg of a hydroxypropylalkylcellulose, selected from the group consisting of hydroxypropylmethylcellulose, hydroxypropylethylcellulose, hydroxypropylbutylcellulose and hydroxypropylhexylcellulose; 0 to 5 mg of an antioxidant, selected from the group consisting of d-alpha tocopherol, dl-alpha tocopherol, d-alpha tocopherol acetate, dl-alpha tocopherol acetate, d-alpha tocopherol acid succinate, dl-alpha tocopherol acid succinate, ascorbyl palmitate, butylated hydroxyanisole, butylated hydroxytoluene and propyl gallate; and 0.1 to 7.5 mg of a lubricant, selected from the group consisting of magnesium stearate, calcium stearate, corn starch, potato starch, bentonite, citrus pulp and stearic acid.

Example 12

A novel therapeutic composition comprising the opiate analgesic, wherein the opiate analgesic is a member selected from the group consisting of morphine, hydromorphone, codeine and hydrocodone, is prepared as follows: first, 52.5 g of opiate analgesic, 82.5 g of poly(ethylene oxide) of 200,000 number-average molecular weight, available from Union Carbide Co., Institute, W. Va., and 9 g of poly(vinyl pyrrolidone) having a viscosity-average molecular weight of 40,000, available from ISP Technologies, Texas City, Tex., are blended homogeneously in a blender at low speed for two minutes. Next, 1.1 g of polysorbate 80 oleate ester, a nonionic surfactant manufactured by Emulsion Engineering Inc., Sanford, Fla., and 30 ml of anhydrous ethanol are blended for approximately one minute, followed by blending all the ingredients slowly to produce a homogenous composition. The composition is dried overnight and then passed through a 0.0331 in. (0.84 mm) screen. Then 1.5 g of lubricant magnesium stearate is blended into the composition for approximately one minute. Next, the composition is compressed into a tablet adapted as a layer for use in a dosage form, under one-ton compression force, with each tablet comprising 357 mg of the opiate analgesic composition. The 357 mg composition comprises 36 wt % opiate analgesic, 57 wt % poly(ethylene oxide), 6 wt % poly(vinyl pyrrolidone), 0.75 wt % polysorbate 80 and 0.25 wt % magnesium stearate.

An osmotic composition possessing aqueous and biological fluid-imbibing expansion properties is prepared as follows: first 146.9 g of poly(carboxymethyl cellulose) selected from the group consisting of sodium carboxymethylcellulose and potassium carboxymethylcellulose of 700,000 weight-average molecular weight, available from Aqualon Co., Hopewell, Va.; 75 g of a bicarbonate, selected from the group consisting of sodium bicarbonate and potassium bicarbonate; 12.5 g of hydroxypropylmethylcellulose of 11,200 number-average molecular weight, available from Dow Chemical Co., Medland, Mich.; 12.5 g of hydroxypropylcellulose of 80,000 viscosity-average molecular weight; and 2.5 g of red ferric oxide are blended at low speed for three minutes to produce a homogenous blend. Then, 100 ml of anhydrous ethanol is added to the dry blend, and all the ingredients blended for two minutes at low speed to yield a wet granulation. The wet granulation is passed through a 0.0469 in. (1.19 mm) screen. The screened granulation is dried overnight and then rescreened through a 0.0331 in. (0.84 mm) screen. Finally, 0.625 g of lubricant, selected from the group consisting of magnesium stearate, stearic acid, and magnesium oleate is blended into the screened granulation for one minute to produce the osmotic composition. The composition is compressed into 238-mg tablets, comprising 139.8 mg of poly(carboxymethylcellulose), 71.4 mg of bicarbonate, 11.9 mg of hydroxypropylmethylcellulose, 11.9 mg of hydroxypropylcellulose, 2.4 mg of ferric oxide and 0.6 mg of lubricant.

A dosage form is provided by the invention as follows: first, the opiate morphine tablets and the osmotic tablets are compressed in contacting layered arrangement to provide a bilayered core. The bilayered core is coated with a semipermeable wall forming composition. The semipermeable membrane-forming composition comprises 95:5 (weight:weight) cellulose acetate having an acetyl content of 39.8% and polyethylene glycol having an average-molecular weight of 3,350. The two composition-forming components are dissolved in 95:5 (weight:weight) mixture of an acetone and water at 4% solid. The average wet semipermeable membrane surrounding the core was 30 mg. Three 30 mil (0.76 mm) orifices are drilled through the semipermeable membrane, connecting the opiate analgesic composition with the exterior of the dosage form. Finally, the dosage forms are dried overnight at 45° C. The dosage forms have an opiate analgesic average mean release rate of 5.5 mg/hr with a nominal T90 of 19 hours.

Example 13

The procedure set forth in the above examples is followed to provide a displacement composition comprising 30 to 375 mg of poly(ethylene oxide) of 3,000,000 to 10,000,000 number-average molecular weight; 25 ng to 150 mg of sodium bicarbonate or potassium bicarbonate; 1 to 60 mg of hydroxypropylmethylcellulose of 9,200 to 75,000 number-average molecular weight; 0.01 to 7.5 mg of a colorant, such as ferric oxide; 0.01 to 3.0 mg of a lubricant, such as magnesium stearate; and 0.01 to 3.5 mg of a nonionic surfactant, such as polysorbate 80 oleate ester.

Example 14

The procedure set forth in the above examples is followed to provide a displacement composition comprising 30 to 375 mg of poly(ethylene oxide) of 3,000,000 to 10,000,000 number-average molecular weight; 25 ng to 150 mg of sodium bicarbonate or potassium bicarbonate; 1 to 60 mg of hydroxypropylmethylcellulose of 9,200 to 75,000 number-average molecular weight; 0.01 to 7.5 mg of a colorant, such as ferric oxide; 0.01 to 3.0 mg of a lubricant, such as magnesium stearate; and 0.01 to 0.5 mg of a nonionic antioxidant, such as butylated hydroxytoluene.

Example 15

A dosage form adapted, designed and shaped as an osmotic drug delivery device was manufactured as follows: first, 50,000 g of morphine sulfate pentahydrate, 66,250 g of pharmaceutically acceptable poly(ethylene oxide) comprising a 200,000 number-average molecular weight, and 5000 g of poly(vinyl pyrrolidone) having a viscosity-average molecular weight of 40,000 were added to the bowl of a Glaft Fluid Bed Granulator®. The bowl was attached to the granulator and the granulation process initiated for effecting granulation. Next, the dry powders were air suspended and mixed for three minutes. Then, a solution prepared by dissolving 3500 g of poly(vinyl pyrrolidone) having a viscosity-average molecular weight of 40,000 in 46,500 g of purified water was sprayed from three nozzles onto the powder. The granulating conditions were monitored during the process as follows: total solution spray rate of approximately 800 g/min, inlet temperature of approximately 40° C., and process air flow of approximately 4000 m$^3$/hr.

While spraying the binder solution, the filter bags were shaken for ten seconds every 1.5 minutes to unglue any possible powder deposits. At the end of the solution spraying 35,700 g, the coated granulated particles were continued with the drying process for approximately 20 minutes. The machine was turned off and the coated granules were removed from the granulator. The coated granules were sized using a fluid air mill with a seven mesh screen (0.111 in. or 2.81 mm). The granulation was transferred to a tumbler, first mixed with 62.5 g of butylated hydroxytoluene, and then mixed and lubricated with 1187 g of magnesium stearate.

Next, a push composition was prepared as follows: 36,000 g of sodium bicarbonate was sized using a Quadro Comil® with a 21-mesh screen. Next, 1200 g of ferric oxide was sized using a 21-mesh screen. Then, all the screened materials, 76,400 g of pharmaceutically acceptable poly(ethylene oxide) comprising a 7,000,000 number-average molecular weight, 3000 g of hydroxypropylmethylcellulose comprising a number-average molecular weight of 11,200 and 1200 g of ferric oxide were added to a granulator's bowl. The bowl was attached to the granulator and the granulation process initiated for effecting granulation. Next, the dry powders were air suspended and mixed for three minutes. Then, a solution prepared by dissolving 4000 g of hydroxypropylmethylcellulose possessing a number-average molecular weight of 11,200 in 46,000 g of water was sprayed from three nozzles onto the powder. The granulating conditions were monitored during the process as follows: total solution spray rate of approximately 700 g/min, inlet temperature of approximately 42° C., and process air flow of approximately 4000 m$^3$/hr.

While spraying the binder solution, the filter bags were shaken for ten seconds every 1.5 minutes to unglue any possible powder deposits. At the end of the solution spraying 37,500 g, the coated granulated particles were continued with the drying process for approximately ten minutes. The machine was turned off, and the coated granules were removed from the granulator. The coated granules were sized with an 8-mesh screen (0.0937 in. or 2.4 mm). The granulation was transferred to a tumbler, first mixed with 99.6 g of butylated hydroxytoluene and then mixed and lubricated with 300 g of magnesium stearate.

Next, the morphine sulfate pentahydrate drug composition and the push composition were compressed into bilayer tablets on a tablet press. First, 284 mg of the morphine sulfate pentahydrate composition was added to the die cavity and precompressed; then, 189 mg of the push composition was added, and the layers pressed under a pressure head of approximately 1500 pounds into a 13/32 in. (1.0 cm), round, contacting layered arrangement.

The bilayered arrangements were coated with a semipermeable wall. The wall-forming composition comprises 95% cellulose acetate having a 39.8% acetyl content, and 5% polyethylene glycol having a viscosity-average molecular weight of 3,350. The wall-forming composition was dissolved in an acetone:water (95:5 wt:wt) cosolvent to make a 4% solids solution. The wall-forming composition was sprayed onto and around the bilayers in a 24 in. coater.

Next two 25 mil (0.64 mm) exit passageways were drilled through the semipermeable wall to connect the drug layer with the exterior of the dosage system. The residual solvent was removed by drying for 48 hours at 45° C. and 45% humidity. Next, the osmotic systems were dried for four hours at 45° C. to remove excess moisture. The dosage form produced by this manufacture provides 40.0% morphine sulfate pentahydrate, 53.0% poly(ethylene oxide) possessing a 200,000 number-average molecular weight, 6% poly(vinyl pyrrolidone) possessing a 40,000 viscosity-average molecular weight, 0.95% magnesium stearate, and 0.05% butylated hydroxytoluene. The push composition comprises 63.67% poly(ethylene oxide) comprising a 7,000,000 number-average molecular weight, 30% sodium bicarbonate, 5% hydroxypropylmethylcellulose comprising a 11,200 number-average molecular weight, 1% green ferric oxide, 0.25% magnesium stearate, and 0.08% butylated hydroxytoluene. The semipermeable wall comprises 95 wt % cellulose acetate comprising a 39.8% acetyl content, and 5.0 wt % polyethylene glycol comprising a 3,350 viscosity-average molecular weight. The dosage form comprised two 25-mil (0.64-mm) passageways, and it had a morphine sulfate mean-release rate of 7 mg/hr.

Example 16

A dosage form adapted, designed and shaped as a drug delivery device was manufactured as follows: first, 50,000 g of morphine sulfate pentahydrate, 66,250 g of pharmaceutically acceptable poly(ethylene oxide) comprising a 200,000 number-average molecular weight, 5000 g of poly(vinyl pyrrolidone), identified as K29-32, having a viscosity-average molecular weight of 40,000 are added to the bowl of a Glatt Fluid Bed Granulator. The bowl was attached to the granulator and the granulation process initiated for effecting granulation. Next, the dry powders were air suspended and mixed for three minutes. Then, a solution prepared by dissolving 3500 g of poly(vinyl pyrrolidone), identified as K29-32, having a viscosity-average molecular weight of 40,000 in 46,500 g of water was sprayed from three nozzles onto the powder. The granulating conditions were monitored during the process as follows: total solution spray rate of approximately 800 g/min, inlet temperature of approximately 40° C., and process air flow of approximately 4000 m$^3$/hr.

While spraying the binder solution, the filter bags were shaken for ten seconds every 1.5 minutes to unglue any possible powder deposits. At the end of the solution spraying 35,700 g, the coated granulated particles were continued with the drying process for approximately 20 minutes. The machine was turned off and the coated granules were removed from the granulator. The coated granules were sized using a fluid air mill with a 7-mesh screen (0.111 in. or 2.81 mm). The granulation was transferred to a Tote Tumbler®, first mixed with 62.5 g of butylated hydroxytoluene and then mixed and lubricated with 1187 g of magnesium stearate.

Next, a push composition was prepared as follows: 1200 g of ferric oxide was sized using a Quadro Comil and a 20-mesh screen. Then, the screened ferric oxide, 112,400 g of pharmaceutically acceptable poly(ethylene oxide) comprising a 7,000,000 number-average molecular weight and 3600 g of hydroxypropylmethylcellulose comprising a number-average molecular weight of 11,200 were added to the bowl of a Glatt Fluid Bed Granulator. The bowl was attached to the granulator and the granulation process initiated for effecting granulation. Next, the dry powders were air suspended and mixed for three minutes. Then, a solution prepared by dissolving 3200 g of hydroxypropylmethylcellulose possessing a number-average molecular weight of 11,200 in 36,800 g of water was sprayed from three nozzles onto the powder. The granulating conditions were monitored during the process as follows: total solution spray rate of approximately 700 g/min, inlet temperature of approximately 45° C., and process air flow of approximately 4000 m$^3$/hr.

While spraying the binder solution, the filter bags were shaken for ten seconds every 1.5 minutes to unglue any possible powder deposits. At the end of the solution spraying 30,000 g the coated granulated particles were continued with the drying process for approximately ten minutes. The machine was turned off and the coated granules were removed from the granulator. The coated granules were sized using a Quadro Comil with an 8-mesh screen (0.0937 in. or 2.4 mm). The granulation was transferred to a Tote Tumbler, first mixed with 99.6 g of butylated hydroxytoluene, and then mixed and lubricated with 300 g of magnesium stearate.

Next, the morphine sulfate pentahydrate drug composition and the push composition were compressed into bilayer tablets on the Manesty® BB4 tablet press. First, 284 mg of the morphine sulfate pentahydrate composition was added to the die cavity and precompressed; then, 189 mg of the push composition was added and the layers were pressed under a pressure head of approximately 1500 pounds into a 13/32 in. (1.0 cm), round, contacting layered arrangement. The bilayered arrangements were coated with a semipermeable wall. The wall-forming composition comprises 95% cellulose acetate having a 39.8% acetyl content and 5% polyethylene glycol having a molecular weight of 3,350. The wall-forming composition was dissolved in an acetone:water (95:5 wt:wt) cosolvent to make a 4% solids solution. The wall-forming composition was sprayed onto and around the bilayers in a 24 in. Vector Hicoater®.

Next, one 25-mil (0.64-mm) exit passageway was mechanically drilled through the semipermeable wall to connect the drug layer with the exterior of the dosage system. The residual solvent was removed by drying for 48 hours at 45° C. and 45% humidity. Next the osmotic systems were dried for four hours at 45° C. to remove excess moisture. The dosage form produced by this manufacture provides 40.0% morphine sulfate pentahydrate, 53.0% poly (ethylene oxide) possessing a 200,000 number-average molecular weight, 6% poly(vinyl pyrrolidone) possessing a 40,000 viscosity-average molecular weight, 0.95% magnesium stearate, and 0.05% butylated hydroxytoluene. The push composition comprises 93.67% poly(ethylene oxide) comprising a 7,000,000 number-average molecular weight, 5% hydroxypropylmethylcellulose comprising a 11,200 number-average molecular weight, 1% green ferric oxide, 0.25% magnesium stearate, and 0.08% butylated hydroxytoluene. The semipermeable wall comprises 95 wt % cellulose acetate comprising a 39.8% acetyl content, and 5.0 wt % polyethylene glycol comprising a 3,350 molecular weight. The dosage form comprises one 25-mil (0.64-mm) passageway and it has a morphine sulfate mean-release rate of 6 mg/hr.

FURTHER DESCRIPTION OF THE INVENTION

The expression "exit means" for the dosage form as used comprises means and methods suitable for the metered release of beneficial drug morphine from the dosage form. The exit means comprises at least one passageway, orifice or the like, through the wall for communicating with morphine in the dosage form. The expression "at least one passageway" comprises aperture, orifice, bore, pore, micropore, porous element through which the drug can migrate, hollow fiber, capillary tube, porous overlay, porous insert, and the like. The expression also includes a material that erodes or is leached from the wall in the fluid environment of use to produce at least one passageway in the dosage form. Representative materials suitable for forming at least one passageway, or a multiplicity of passageways, include an erodible/poly(glycolic) acid or poly(lactic) acid member in the wall, a gelatinous filament, poly(vinyl alcohol), leachable materials such as fluid-removable pore-forming polysaccharides, salts, oxides, and the like. A passageway, or a plurality of passageways, can be formed by leaching a material, such as sorbitol, lactose, fructose and the like, from the wall. The passageway can have any shape, such as round, triangular, square, elliptical and the like, for assisting in the metered release of morphine from the dosage form. The dosage form can be constructed with one or more passageways in spaced apart relations, or more than one passageway on a single surface of a dosage form. Passageways and equipment for forming passageways are disclosed in U.S. Pat. Nos. 3,845,770; 3,916,899; 4,063,064 and 4,088,864. Passageways formed by leaching are disclosed in U.S. Pat. Nos. 4,200,098 and 4,285,987.

Exemplary solvents used for the present purpose comprise inorganic and organic solvents that do not adversely harm the materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl either, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclo-yexane, cyclo-octane, benzene, toluene, naphtha, a, 4-dioxane, tetrahydrofurna, diglyme, aqueous and nonaqueous mixtures thereof, such as acetone and water, acetone and methanol, acetone and ethyl alcohol, methylene dichloride and methanol, and ethylene dichloride and methanol.

DISCLOSURE FOR USING THE INVENTION

The invention concerns also a method for administering 50 ng to 1,000 mg of an opiate analgesic or a non-opiate analgesic to a patient, wherein said method comprises orally admitting into the patient 50 ng to 1,000 mg of a member selected from the group consisting of an opiate analgesic and non-opiate analgesic, and a nonionic surfactant. The method provides additionally administering 50 ng to 1,000 mg of the opiate analgesic or non-opiate analgesic to a patient from a dosage form comprising a semipermeable wall permeable to the passage of an aqueous-biological fluid and impervious to the passage of said analgesic. The dosage form comprises the analgesic composition and an osmotic push composition surrounded by a semipermeable wall, and exit means in the wall for delivering the analgesic from the dosage form by imbibing fluid through the wall into the dosage from causing the analgesic composition to change to a wet dispensable form, and causing the push composition to expand and push the analgesic composition through the exit means, whereby through the combined operations of the dosage form the analgesic is delivered at a therapeutically effective dose at a controlled rate over a sustained period of time up to 28 hours.

Inasmuch as the foregoing specification comprises disclosed embodiments, it is understood what variations and modifications may be made herein, in accordance with the principles disclosed, without departing from the invention.

We claim:

1. An osmotic composition comprising 30 to 225 mg of a member selected from the group consisting of sodium carboxymethylcellulose, potassium carboxymethylcellulose and calcium carboxymethylcellulose of 75,000 to 2,500,000 molecular weight, 25 to 150 mg of a member selected from the group consisting of a alkali metal carbonate, alkali metal bicarbonate, alkaline earth carbonate and alkaline earth bicarbonate, 1 to 30 mg of hydroxypropylmethylcellulose of 9,200 to 125,000 molecular weight, 1 to 30 mg of hydroxypropylcellulose of 7,500 to 125,000 molecular weight and 0.1 to 3 mg of a lubricant.

2. A bilayer tablet comprising a first layer comprising 50 ng to 1000 mg of an opiate analgesic, 35 to 275 mg of a poly(alkylene oxide) of 100,000 to 650,000 molecular weight, 0.5 to 50 mg of a poly(vinyl pyrrolidone) of 7,500 to 225,000 molecular weight, 0.1 to 10 mg of a lubricant selected from the group consisting of magnesium stearate, calcium stearate, potassium oleate, and sodium stearate; and a second layer comprising 30 to 225 mg of a carboxymethylcellulose of 75,000 to 2,500,000 molecular weight, 25 to 150 mg of a member selected from the group consisting of lithium carbonate, sodium carbonate, potassium carbonate, lithium bicarbonate, sodium bicarbonate, potassium bicarbonate, and magnesium bicarbonate, 1 to 30 mg of a hydroxypropylmethylcellulose of 9,200 to 125,000 molecular weight and 1 to 30 mg of a hydroxypropylcellulose of 7,500 to 125,000 molecular weight.

3. A bilayer tablet comprising a first layer comprising 50 ng to 1,000 mg of a opiate analgesic, 35 to 275 mg of a poly(alkylene oxide) of 100,000 to 650,000 molecular weight, 0.5 to 50 mg of a poly(vinyl pyrrolidone) of 7,500 to 225,000 molecular weight, and 0.01 to 0.5 mg of an antioxidant; and a second layer comprising 30 to 375 mg of a poly(alkylene oxide) of 3,000,000 to 10,000,000 molecular weight, 25 to 150 of a member selected from the group consisting of a carbonate and bicarbonate, 1 to 60 mg of a hydroxypropylmethylcellulose of 9,200 to 125,000 molecular weight and 0.01 to 3 mg of an antioxidant.

4. A bilayer tablet comprising a first layer comprising 50 ng to 1,000 mg of a non-opiate analgesic selected from the group consisting of alfentanil, ketoprofen, buprenorphine, butorphanol, fentanyl, meperidine, methadone, nalbuphine, propoxyphene, natrexone, pentazocine, sufentanil, acetaminophen, aspirin, ibuprofen, and naproxen, 35 to 275 mg of a poly(ethylene oxide) of 100,000 to 650,000 molecular weight, 0.5 to 50 mg of a poly(vinyl pyrrolidone) of 7,500 to 225,000 molecular weight, and 0 to 10 mg of a nonionic surfactant; and second layer possessing aqueous-fluid imbibing property comprising 30 to 225 mg of a carboxymethylcellulose of 75,000 to 2,500,000 molecular weight, 25 to 150 mg of a member selected from the group consisting of lithium carbonate, sodium carbonate, potassium carbonate, lithium bicarbonate, sodium bicarbonate, potassium bicarbonate, and magnesium bicarbonate, 1 to 30 mg of a hydroxypropylalkylcellulose of 9,200 to 125,000 molecular weight, and 1 to 30 mg of a hydroxypropylcellulose of 7,500 to 125,000 molecular weight, and 0 to 5 mg of an antioxidant.

5. A bilayer tablet comprising a first layer comprising 50 ng to 1,000 mg of a non-opiate analgesic selected from the group consisting of alfentanil, ketoprofen, buprenorphine, butorphanol, fentanyl, meperidine, methadone, nalbuphine, propoxyphene, natrexone, pentazocine, sufentanil, acetaminophen, aspirin, ibuprofen, and naproxen, 35 to 275 mg of a poly(ethylene oxide) of 100,000 to 650,000 molecular weight, 0.5 to 50 mg of a poly(vinyl pyrrolidone) of 7,500 to 225,000 molecular weight, and 0 to 10 mg of a nonionic surfactant; and second layer possessing aqueous-fluid imbibing properties consisting of 30 to 375 mg of a poly(alkylene oxide) possessing a 3,000,000 to 10,000,000 molecular weight, 25 to 150 mg of a member selected from the group consisting of lithium carbonate, sodium carbonate, potassium carbonate, lithium bicarbonate, sodium bicarbonate, potassium bicarbonate, and magnesium bicarbonate, 1 to 60 mg of a hydroxypropylalkylcellulose of 9,200 to 125,000 molecular weight, 0 to 60 mg of a hydroxypropylcellulose of 7,500 to 125,000 molecular weight, and 0.01 to 3 mg of an antioxidant.

* * * * *